United States Patent [19]

Cohen et al.

[11] 4,226,593
[45] Oct. 7, 1980

[54] APPARATUS AND METHOD FOR APPLYING DENTAL VENEER

[76] Inventors: Morton Cohen, 1555 W. Main St., Norristown, Pa. 19401; Elliott Silverman, 4829 Atlantic Ave., Ventnor, N.J. 08406

[21] Appl. No.: 30,005

[22] Filed: Apr. 16, 1979

[51] Int. Cl.³ ............................................. A61C 5/00
[52] U.S. Cl. ...................................... 433/217; 433/37
[58] Field of Search ............... 433/217, 222, 223, 218, 433/36, 37, 47, 34; 264/16, 19

[56] References Cited

U.S. PATENT DOCUMENTS

| | | | |
|---|---|---|---|
| 1,507,476 | 9/1924 | Flanigan | 433/223 |
| 2,754,592 | 7/1956 | Jankelson | 433/34 |
| 3,004,343 | 10/1961 | Rydin | 433/217 |
| 3,375,582 | 4/1968 | Myerson | 433/223 |
| 3,738,005 | 6/1973 | Cohen et al. | 433/24 |
| 3,763,564 | 10/1973 | Petrelli et al. | 433/217 |
| 3,986,261 | 10/1976 | Faunce | 433/217 |
| 3,987,545 | 10/1976 | Kennedy | 433/36 |

*Primary Examiner*—Robert Peshock
*Assistant Examiner*—John J. Wilson
*Attorney, Agent, or Firm*—Robert K. Youtie

[57] ABSTRACT

A dental method and apparatus wherein a plurality of tooth covers, shells, laminates or veneers are suitably configured for respective congruent facing relation with the labial surfaces of a patient's dental cast teeth, removably affixed thereto, and encompassed by a flexible mold for removal from the dental cast and transfer in proper orientation to the patient's teeth for securement thereto of the veneers and removal from the veneers of the mold.

14 Claims, 8 Drawing Figures

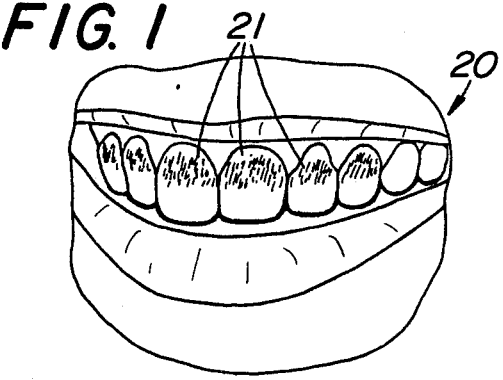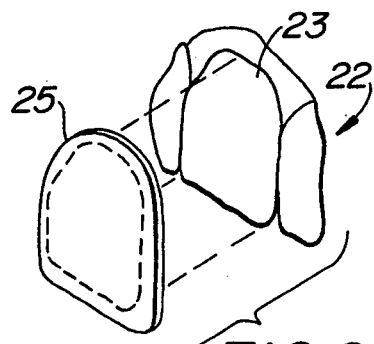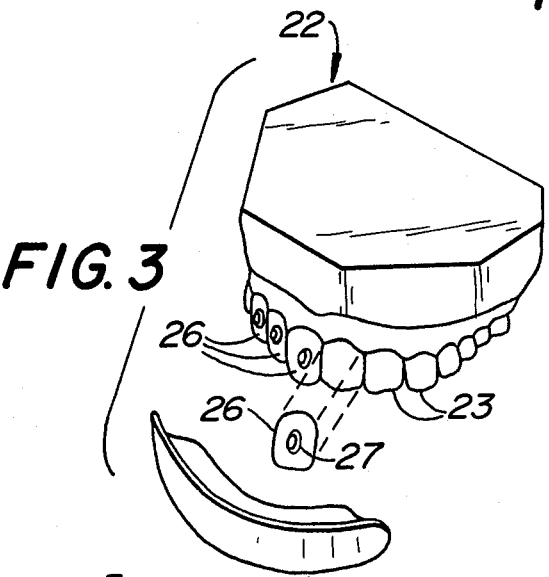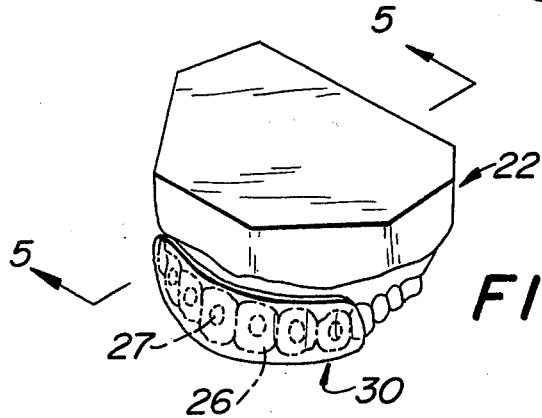

U.S. Patent    Oct. 7, 1980    Sheet 2 of 2    4,226,593
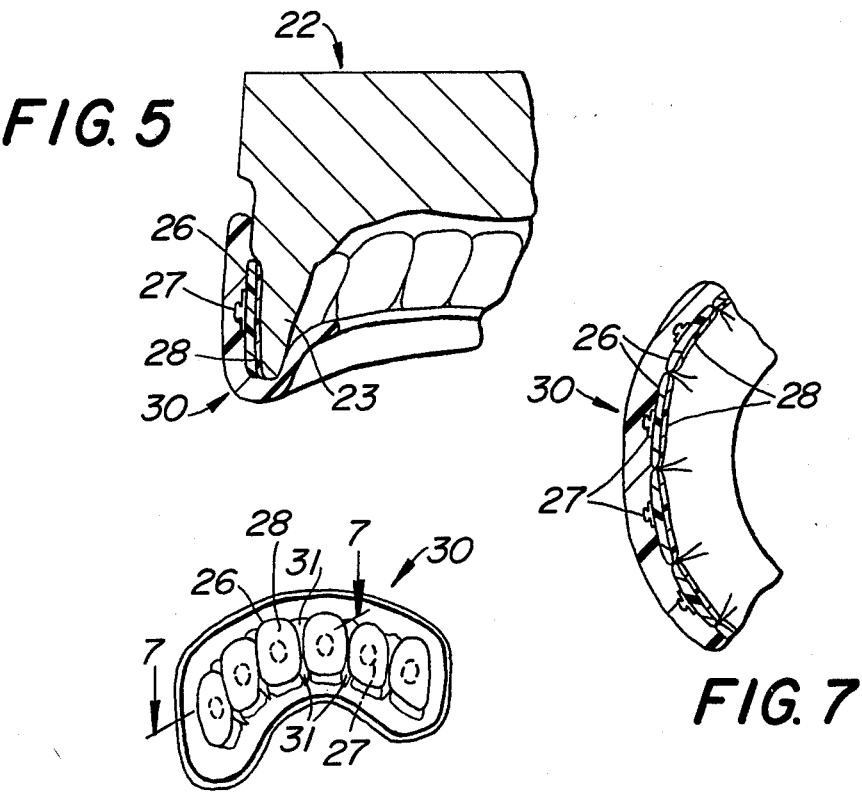
FIG. 5
FIG. 7
FIG. 6
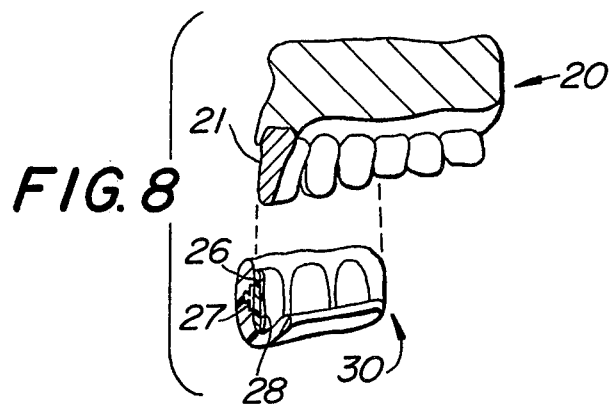
FIG. 8

APPARATUS AND METHOD FOR APPLYING DENTAL VENEER

BACKGROUND OF THE INVENTION

There is known in the dental arts the application to patient's teeth of a covering laminate, veneer or shell, both for cosmetic and curative purposes. However, such practices have heretofore required of the dentist very considerable time with and discomfort to the patient. Particularly prior tooth veneer or laminate apparati and procedures have required of the dentist a relatively high degree of skill in shaping of the veneers to precise conformation with the tooth contours, and also have required of the dentist the use of unduly large amounts of adhesive to assure the desired total veneer facing engagement with its associated tooth, necessarily resulting in relatively large excesses of adhesive material extruded or expressed beyond the veneer onto adjacent surfaces and requiring removal therefrom. An example of such materials and procedure is that currently sold by the Caulk Division of Dentsply International Inc., under the trademark Mastique.

The present invention is concerned broadly with the simultaneous transfer of a plurality of dental appliances from precisely positioned locations on a dental model to corresponding locations in the patient's mouth, and the only known prior art concerned with the simultaneous transfer and positioning of dental appliances is that of U.S. Pat. No. 3,738,005 to Cohen et al.

SUMMARY OF THE INVENTION

It is an important object of the present invention to provide a dental method and apparatus for the application of tooth veneers, as in the treatment of malformed, stained, hypoplastic and fractured teeth, which overcome the above mentioned difficulties, effect very substantial reduction in chair time, patient discomfort and expense; provide a greatly improved result without the exercise of more than ordinary skill; and wherein minimal amounts of adhesive material are required to be used by the dentist to effectively minimize the expression of excess and its necessary removal.

It is another object of the present invention to provide unique improvements in a dental method and apparatus for applying tooth veneers, wherein a substantial part of the procedure may be performed by laboratory technicians in the absence of the patient to effect substantial savings in cost and convenience, and wherein there is provided receiving means for any excess adhesive material expressed from between the patient's teeth and veneers so as to avoid any distortion or other deleterious effects by excess adhesive, while permitting the latter to be more readily removed and assuring full adhesive occupancy of the space between teeth and veneers.

Other objects of the present invention will become apparent upon reading the following specification and referring to the accompanying drawings, which form a material part of this disclosure.

The invention accordingly consists in the features of construction, combinations and arrangements of parts and method steps, which will be exemplified in the following description, and of which the scope will be indicated by the appended claims.

BRIEF DESCRIPTION OF THE DRAWINGS

FIG. 1 is a front perspective view showing the teeth of a patient to be covered by veneers in accordance with the teachings of the instant invention.

FIG. 2 is an exploded partial perspective view showing a tooth of a dental cast and illustrating an early stage of the present invention.

FIG. 3 is an exploded perspective view showing a dental cast as employed in a slightly later stage of the invention.

FIG. 4 is a perspective view showing a dental cast and mold in still a later stage of the present invention.

FIG. 5 is a sectional view taken generally along the line 5—5 of FIG. 4.

FIG. 6 is an internal perspective view showing the mold of FIGS. 4 and 5, removed therefrom and inverted to show the veneers on the interior of the mold.

FIG. 7 is a sectional view taken generally along the line 7—7 of FIG. 6.

FIG. 8 is a sectional elevational view showing a patient's teeth and the mold assembly of FIGS. 6 and 7 preparatory to application to the teeth.

DESCRIPTION OF THE PREFERRED EMBODIMENT

Referring now more particularly to the drawings, and specifically to FIGS. 1-4 thereof, in FIG. 1 there is shown a pateint's mouth generally designated 20, and illustrating the labial surfaces of the anterior teeth 21. For purposes of illustration, the patient's teeth are shown as being stained, and therefore desirably covered by tooth veneers or laminates. In conventional manner there is formed a dental cast or model, as at 22, providing an accurate reproduction of the patient's teeth, as by the cast teeth 23.

A veneer blank or shell is shown in FIG. 2 at 25, being fabricated of clear or light permeable plastic and selected for its approximate size corresponding to the size of the patient's corresponding tooth 21.

A lab technician, having been instructed by the dentist at least as to the size of veneer blank 25, then proceeds to shape the veneer blank into correspondence with the labial surface of the associated tooth 23. As with white stone or other suitable material, the inner surface of the veneer blank 25 is ground or configured into a closely conforming engagement with the labial contour of its associated cast tooth 23. Also, the peripheral margin of the veneer blank 25 is shaped to achieve the desired length and accommodate closely to the gingival margin of the tooth. In general, this is a cut-and-try procedure performed until the veneer is of the desired outline configuration and has its inner surface configured for application to the cast tooth without distention of the veneer. Such a shaped veneer is shown at 26 in FIG. 4. Of course, the working of the veneer blank to its desired shape produces dirt and debris which is necessarily removed from the veneer by a suitable cleaner.

The inner or tooth facing surface of the veneer may then be provided with a thin coat or layer of primer or plasticizer. This primer or plasticizer is allowed to remain for about ten minutes and softens or roughens the inner surface of the veneer 26 to enhance a bond of the inner veneer surface with an adhesive.

A plurality of veneer blanks may be so treated, each shaped for conforming engagement with a respective anterior tooth 23 of the model 22, cleaned and treated with the primer or plasticizer. The dental cast or model 22 is coated with a separating solution or parting agent, that being sold under the trademark Liquid Foil having been found satisfactory. The model or dental cast must be dry to receive the parting agent, a drying period of twenty-four hours being sufficient.

A hardenable fluent material or adhesive, such as that sold by Dentsply International Inc. under the trademark Mastique Shader Paste is applied over the entire inner surface of the shell or veneer 26. The veneer blank 25 and shaped veneer 26 may be fabricated of clear plastic, and colored as desired by the visual presentation therethrough of the selected color of Shader Paste. That is, the Shader Paste is a hardenable fluent adhesive, and further is activatable by ultraviolet light or self-polymerizing to cause the setting or hardening. Each shaped veneer 26 with the hardenable adhesive on its inner side is applied to and held against the corresponding tooth, and ultraviolet light is transmitted through the veneers to harden and set the adhesive. The adhesive completely covers the inner surface of each veneer to eliminate voids and air bubbles for maximum bonding, and the setting of the adhesive produces a firm, strong adherence to the veneer, while producing a less strong or frangible adherence to the cast teeth 23, by reason of the separating or parting agent.

With the veneers 26 thus firmly positioned on the cast teeth 23, a resiliently deflectable tray or mold is formed about the veneers and cast teeth, such as is generally designated 30. Prior to formation of the mold 30 there are advantageously provided on the outer surfaces of respective veneers 26 a holding attachment, as at 27, which may assume a button-like configuration, or other suitable configuration being undercut for capture by the mold material. The attachment members or undercut buttons 27 are each detachably secured, as by suitable adhesive, to the outer surface of a respective veneer 26.

The material of mold 30, which may be silicone, thermoplastic, or any suitable formable material, is formed about the anterior dental cast teeth and the veneers 26 together with the buttons 27, as shown in FIG. 4. This is best seen in FIG. 5, wherein it is apparent that a button 27 includes an enlarged head captured within the material of the mold. Also seen therein is a layer 28 of the hardenable adhesive material interposed between the veneer 26 and dental cast tooth 23. The molding material of mold 30 is of a form retaining, but resiliently deflectable characteristic, such as rubber, in its finally hardened or cured condition.

After curing of the mold 30, the mold, together with the captured buttons 27, and the attached veneers 26 are, as a unit, removed from the dental cast 22. Further, the adhesive layer 28 on the labial surface of veneer 26 remains adhesively affixed to the veneer, and releases from the labial surface of the tooth 23 due to the separating or release agent previously applied to the dental cast teeth. The hardened layer 28 thereby is formed with an exposed surface contour substantially exactly complementary to the labial surface of dental cast tooth 23 and the labial surface of the corresponding patient's tooth.

The removed assemblage of mold 30, with veneers 26, inner layer 28 and attachment members 27 is shown in FIGS. 6 and 7. Provided in the mold 30, see FIG. 6, at locations closely adjacent to each veneer 26, and openings, recesses or receivers 31, for a purpose appearing presently.

In the dental chair the patient's teeth are conditioned for the veneer application, as by suitable etching, drying and the application of a thin sealant layer which may be suitably colored and opaque to cover stains, say self-curing or ultraviolet activated. The specifically contoured layers 28 may then be coated with additional adhesive, say self-curing or ultraviolet activated, and the assemblage of FIGS. 6 and 7 is ready for application to the patient∝s teeth 21, as shown in FIG. 8. That is, the mold 30 is moved to properly locate the several veneers 26 in precise location on the labial surfaces of the patient's teeth 21. A minimum of adhesive may be employed, as the layers 28 are specifically configured for conforming engagement with their respective teeth, so that an extremely thin layer of adhesive will serve to fully occupy the space between the teeth and layers 28, eliminating voids, air bubbles and the like, and assuring maximum bond. Any excess of adhesive expressed beyond the veneers 26 will be received in recesses 31, so as not to distort the mold or dislocate the veneers. This results in a well controlled use of adhesive material, with minimum clean up required.

Activation by ultraviolet light cures the adhesive in firm bonding engagement with both layer 28 and patient's tooth 21, after which the mold 30 may be stripped from the veneers, leaving the latter properly positioned on the teeth. That is, the mold 30 may be flexed to release the holding attachments 27, and the latter may be ground or otherwise removed from the veneers.

As the hardened layer 28 will obscure the fluid adhesive to an activating light, it may be desired to employ a self-curing adhesive between the layer 28 and patient's tooth 23. Also, on very badly stained teeth the dentist may wish to apply an opaque coating prior to application of the veneer to assure the stain is fully hidden. With the self-curing adhesive, it may be necessary to hold the mold or tray 30 in position in the patient's mouth for about five minutes, after which the mold or tray may be removed, as described.

From the foregoing, it is seen that the present invention provides a dental method and apparatus for applying a plurality of veneers to a patient's teeth, which assures a high standard of work as the tedious detail of fitting is done on a dental cast rather than in the mouth, effects substantial savings in costs as the bulk of the labor is done by a lab technician in the lab rather than by the dentist at chair side, and which otherwise fully accomplishes its intended objects.

Although the present invention has been described in some detail by way of illustration and example for purposes of clarity of understanding, it is understood that certain changes and modifications may be made within the spirit of the invention.

What is claimed is:

1. The method of applying a plurality of separate veneers to respective teeth of a patient, which method comprises; making a dental cast of the patient, shaping a plurality of veneers each for generally conforming congruent facing engagement with the labial contour of a respective cast tooth, applying a hardenable fluent material to the entire inner surface of each veneer, placing said veneers in position on the cast teeth to express excess material from between the cast teeth and veneers, removing the excess material, applying removable attachment means on the outer side of each veneer, applying a molding material into conforming engagement with the dental cast and veneers to define a mold having the veneers attached by said attachment means, removing the mold and attached veneers from the dental cast together with the hardenable material hardened to contours precisely conforming to the cast teeth, applying the mold and attached veneers to the patient's teeth to properly position the veneers in precise congruent conforming engagement with the patient's teeth, securing the positioned veneers to the patient's teeth, removing the mold while leaving the veneers secured to the patient's teeth, and removing the attachment means from the veneers.

2. The method according to claim 1, further characterized in applying a parting agent to the labial surface of the cast teeth, said hardenable fluent material being adhesive with a substantial adherence to the veneers and a frangible adherence to the cast teeth by reason of said parting agent.

3. The method according to claim 2, said hardenable fluent material being light activatable adhesive and transmitting activating light to said adhesive before applying the molding material.

4. The method according to claim 3, further characterized in selecting a hardenable fluent material having a color corresponding to that of the contiguous teeth.

5. The method according to claim 2, said veneers being fabricated of plastic, and applying a plasticizer to the inner surface of each veneer prior to the application of said hardenable fluent material for enhanced adherence of the latter to the veneer.

6. The method according to claim 2, said hardenable fluent material be self-polymerizing.

7. The method according to claim 1, further characterized in chemically securing said veneers to the patient's teeth.

8. The method according to claim 1, further characterized in securing said veneers to the patient's teeth by adhesive.

9. The method according to claim 1, further characterized in interposing a chemically adhesive material between the patient's teeth and veneers to effect chemical securement, and providing recesses in the mold adjacent to the veneers to receive excess chemical adhesive material expressed from between said veneers and patient's teeth.

10. The method according to claim 1, further characterized in applying an opaque coating over stains on the patient's teeth before applying the veneers to the patient's teeth.

11. The method according to claim 1, further characterized in applying removable attachment means to the veneers by detachably connecting undercut members to the veneers, for withdrawal of the veneers from the dental cast with the mold and undercut members and removal of the mold and undercut members from the veneers secured to the patient's teeth.

12. Dental apparatus comprising the combination of: a dental cast of a patient, a plurality of tooth veneers each conformably overlying the labial contour of a cast tooth, a quantity of adhesive material sandwiched between each of said veneers and the associated cast tooth to fully occupy the space therebetween, said adhesive material being strongly adhesive to the veneers and weakly adhesive to the cast teeth, removable mold attachment means on the outer side of each veneer, a mold or resilient flexible material in conforming engagement with said dental cast and veneers for removal from said cast teeth together with said veneers attached to said mold by said mold attachment means, said mold and veneers being conformably engagable with the patient's teeth to selectively locate the veneers in precisely conforming relation with the patient's teeth, and adhesive interposed between the veneers and patient's teeth for effecting securement therebetween, whereby said mold is removable from the patient's teeth while leaving the veneers selectively located on the patient's teeth and said attachment means are removable from the veneers.

13. Dental apparatus according to claim 12, said mold being recessed adjacent to said veneers to receive excess adhesive expressed beyond said veneers.

14. Dental apparatus according to claim 12, said attachment means each comprising an undercut member detachably affixed to a veneer for capture and release by said mold.

* * * * *